United States Patent [19]

Mase et al.

[11] Patent Number: 4,728,411

[45] Date of Patent: Mar. 1, 1988

[54] ELECTROCHEMICAL DEVICE

[75] Inventors: Syunzo Mase, Tobishima; Shigeo Soejima, Nagoya, both of Japan

[73] Assignee: NGK Insulators, Ltd., Japan

[21] Appl. No.: 809,745

[22] Filed: Dec. 17, 1985

[30] Foreign Application Priority Data

Dec. 20, 1984 [JP] Japan ................. 59-270043

[51] Int. Cl.$^4$ ............................................ G01N 27/58
[52] U.S. Cl. ..................... 204/425; 204/412; 204/426; 204/427; 204/428; 204/429
[58] Field of Search ............... 204/408, 412, 424, 425, 204/426, 427, 428, 429

[56] References Cited

U.S. PATENT DOCUMENTS

| | | | |
|---|---|---|---|
| 4,272,329 | 6/1981 | Hetrick et al | 204/412 XR |
| 4,282,080 | 8/1981 | Muller et al | 204/412 |
| 4,450,065 | 5/1984 | Yamada et al | 204/426 XR |
| 4,498,968 | 2/1985 | Yamada et al | 204/412 |
| 4,505,806 | 3/1985 | Yamada | 204/427 XR |
| 4,505,807 | 3/1985 | Yamada | 204/412 XR |

Primary Examiner—John F. Niebling
Assistant Examiner—Nam X. Nguyen
Attorney, Agent, or Firm—Parkhurst & Oliff

[57] ABSTRACT

An electrochemical device of a laminar structure for determining the concentration of a component in a measurement gas, comprising: a pumping cell including a first and a second electrode disposed on a first planar solid electrolyte body; a sensing cell including a third and a fourth electrode disposed on a second planar solid electrolyte body; and a thin flat space to which the first and third electrodes are exposed and which communicates with an external space in which the measurement gas exists. The thin flat space has a diffusion resistance to the component in the measurement gas introduced through an inlet thereof. The first and third electrodes and the thin flat space are positioned and dimensioned relative to each other so that a distance "l" is smaller than a distance "m", as measured in a cross section perpendicular to planes of the solid electrolyte bodies, where the distance "l" is measured between the inlet of the thin flat space and a point of the first electrode nearest to the inlet as measured in the above-indicated cross section, and the distance "m" is measured between the inlet and a point of the third electrode nearest to the inlet as measured in the above-indicated cross section.

22 Claims, 9 Drawing Figures

ELECTROCHEMICAL DEVICE

BACKGROUND OF THE INVENTION

1. Field of the Invention

The present invention relates generally to an electrochemical device, and more particularly to improvements in an electrochemical device of laminar structure which comprises an electrochemical cell having a planar solid electrolyte body.

2. Related Art Statement

There are known various electrochemical devices using a solid electrolyte material, for example as oxygen sensors to detect the oxygen concentration in exhaust gases which are emitted from an internal combustion engine of an automotive vehicle. A typical example of such oxygen sensors comprises a body of oxygen-ion conductive solid electrolyte such as zirconia ceramics. This oxygen sensor operates to determine the oxygen concentration according to the principle of an oxygen concentration cell. Also known in the art of electrochemical devices are detectors such as sensing and pumping elements for detecting hydrogen, nitrogen, carbon dioxide, etc. In such type of electrochemical devices, solid electrolyte materials have been used generally in the form of a tubular body which has an elongate bore closed at its one end. Recently, however, there has been an increasing effort to replace the tubular solid electrolyte body with a planar solid electrolyte body, as disclosed in U.S. Pat. Nos. 4,334,974; 4,282,080; and 4,300,990, in view of relatively low productivity and relatively high cost of manufacture of the solid electrolyte bodies of tubular configuration, and from the standpoint of easy assembling of parts with a planar solid electrolyte body. In the case where such planar solid electrolyte bodies are used, suitable electrodes are formed on the surfaces of the solid electrolyte layers, such that the solid electrolyte layers and other layers are stacked on each other into a laminar structure which constitute an electrochemical cell or element.

Generally, an electrochemical cell of the laminar structure indicated above is constituted by a planar solid electrolyte body and at least one pair of electrodes. An electrochemical sensing element of an electrochemical device comprises an electrochemical pumping cell and an electrochemical sensing cell both of which have the laminar structure as described just above. These pumping and sensing cells are superposed on each other, so that the electrochemical sensing element itself has a laminar structure. The laminar sensing element is provided with an internal thin flat measurement-gas space which is formed in communication with an external space in which an exernal measurement gas exists. This internal flat space has a thickness which is determined to provide a predetermined diffusion resistance to the measurement gas. One of the two electrodes of each of the pumping and sensing cells is disposed so that it is exposed to the measurement gas in the flat measurement-gas space. The electrochemical pumping cell performs a pumping function to control the concentration of a given component in the measurement gas within the measurement-gas space. In the meantime, the electrochemical sensing cell serves to measure an electromotive force which is induced between its two electrodes, due to a difference in concentration of the measurement component between the controlled measurement gas within the measurement-gas space and a suitable reference gas.

The inventors of the present invention studied the aforementioned laminar electrochemical element wherein one of the two electrodes of each electrochemical cell is exposed to the flat measurement-gas space. The study revealed an inconvenience that when the measurement gas is an ambient air and the air in the measurement-gas space is controlled by the pumping cell, there exists a difference in concentration of a measurement component between an atmosphere adjacent to the pumping electrode and an atmosphere adjacent to the measuring electrode of the sensing cell, due to a resistance of diffusion in the direction of thickness or depth of the measurement gas space. Consequently, the accuracy of detection is not satisfactory. Further, the electromotive force induced between the electrodes of the sensing cell tends to be extremely small.

An electrochemical element as discussed above is usually used for measuring exhaust gases which are emitted for example by internal combustion engines. If the ambient air is used as a measurement gas, however, a pumping action of the pumping cell of the electrochemical element will not cause the atmosphere within the flat measurement-gas space to become like a rich-burned exhaust gas which is produced as a result of combustion of an air-fuel mixture having an air/fuel ratio lower than the stoichiometric point. Described more specifically, when exhaust gases are introduced as a measurement gas into the flat measurement-gas space, $CO_2$, $H_2O$ and other gases which are contained in the exhaust gases as a result of combustion of an air-fuel mixture are reduced by electrode reaction of the pumping cell, whereby reductive gases are produced within the measurement-gas space. These reductive gases enable the atmosphere in a portion or a major portion of the measurement-gas space to have a relatively low concentration of oxygen. If ambient air is introduced into the measurement-gas space, the oxygen concentration can be held relatively low only in a portion of the measurement-gas space adjacent to the pumping electrode, since nitrogen is a major component of the ambient air, other than oxygen.

For the above reason, it is impossible to use ambient air as a test gas for testing the electrochemical element, in an industrial production of electrochemical devices, to check for the diffusion resistance of its measurement-gas space, that is, the limiting current of the pumping cell. Therefore, it is assumed that the testing of the electrochemical element requires a specially designed complicated device for producing a test gas in which the electrochemical element is checked for its pumping performance.

In addition, even after the electrochemical device is installed as an oxygen sensor on an automotive vehicle, it is necessary to conduct a periodic test of the electrochemical element to check for deterioration of its pumping capability or performance during its service, and to adjust the oxygen sensor as needed, to permit the sensor to perform an accurate sensing operation. Since ambient air can not be used as a test gas as previously indicated, it is almost impossible to test the oxygen sensor while it is installed on the vehicle.

SUMMARY OF THE INVENTION

It is therefore an object of the present invention to provide an electrochemical device, for measuring an oxygen partial pressure in particular, which permits an improved accuracy of measurement and which is highly responsive to ambient air as a test gas, enabling the sensing cell to provide a sufficiently high level of electromotive force while the introduced ambient air is controlled by the pumping cell, and thereby permitting a test of the electrochemical element by using the ambient air.

According to the present invention, there is provided an electrochemical device of a laminar structure for determining the concentration of a component in a measurement gas, including (a) an electrochemical pumping cell having a first planar solid electrolyte body, and at least one pair of electrodes consisting of a first electrode and a second electrode which are disposed in contact with the first planar solid electrolyte body; (b) an electrochemical sensing cell having at least one pair of electrodes consisting of a third electrode and a fourth electrode which are disposed in contact with the second planar solid electrolyte body; and (c) means defining a thin flat measurement-gas space communicating with an external space in which the measurement gas exists, the measurement-gas space having a predetermined diffusion resistance to the component in the measurement gas which is introduced through an inlet of the measurement-gas space, the first electrode of the electrochemical pumping cell and the third electrode of the electrochemical sensing cell being substantially exposed to the measurement-gas space, characterized in that the first electrode, the third electrode and the measurement-gas space are positioned and dimensioned relative to each other so that a distance "l" is smaller than a distance "m", as measured in a cross section perpendicular to planes of the first and second planar solid electrolyte bodies, where the distance "l" is measured between the inlet of the measurement-gas space and a point of the first electrode nearest to the inlet as measured in the above-indicated cross section, and the distance "m" is measured between the inlet and a point of the third electrode nearest to the inlet as measured in the same cross section.

In the electrochemical device of the present invention constructed as described above, the third electrode of the sensing cell which is exposed to the measurement-gas space having the predetermined diffusion resistance, is positioned a greater distance away from the inlet of the measurement-gas space, than the first electrode of the pumping cell. This arrangement effectively prevents the third electrode of the sensing cell from being influenced by a gradient of concentration of the measurement component within the measurement-gas space, which gradient is caused by a pumping action of the pumping cell for pumping out the measurement component in the measurement gas which is diffused into the measurement-gas space. Consequently, the level of an electromotive force induced by the sensing cell is made relatively high, which permits reliable detection of the measurement gas with an improved accuracy.

If ambient air is introduced as the measurement gas into the measurement-gas space in an electrochemical device wherein the first electrode of the pumping cell and the third electrode of the sensing cell substantially entirely overlap with each other as viewed in the direction of thickness of the cells, only oxygen is pumped out into the external space by the pumping cell because the major components in the ambient air diffused into the measurement-gas space are oxygen and nitrogen. Although the atmosphere within the measurement-gas space may be controlled to have a very low oxygen concentration, it is impossible that the atmosphere in the measurement-gas space has a composition similar to a rich-burned exhaust gas previously indicated. Therefore, an amount of oxygen which is diffused from the external space into the measurement-gas space, and an amount of oxygen which is pumped out by the pumping cell, are the only factors which establish a gradient of oxygen concentration in the measurement-gas space, in which the oxygen concentration is reduced in the direction from the inlet of the measurement-gas space toward its innermost portion. In this condition, the third electrode is exposed to both an atmosphere of a relatively high oxygen concentration and to a neutral or stoichiometric atmosphere. Namely, there always remains a small amount of oxygen in average over the entire surface of the third electrode. Consequently, a difference in oxygen concentration between the atmosphere contacting the third electrode, and the reference gas is not sufficient for inducing a high level of electromotive force between the third and fourth electrodes of the sensing cell.

To augment the above-indicated advantages of the present invention, it is preferred that the distance "l" of the first electrode and the distance "m" of the third electrode are determined so as to satisfy the following dimensional relation:

$$m - l \geq 5w,$$

where, w: distance between surfaces of the first and third electrodes which are exposed to the measurement-gas space.

FIG. 9 shows relations between a pumping current Ip applied to the electrochemical pumping cell, and an electromotive force Vs induced in the electrochemical sensing cell, when an ambient air is used as a measurement gas. The Ip—Vs curves indicated in the figure were obtained on different electrochemical devices whose values "m−l" are 0, w, 3w, 5w and 10w. As is understood from the graph in FIG. 9, it is desired that the distances "l" and "m" satisfy the above dimensional relation, to permit the sensing cell to induce a sufficiently high level of electromotive force even when the ambient air is used as the measurement gas, i.e., as a test gas.

Described in more detail, the measurement component in the measurement gas which is diffused into the measurement-gas space through the inlet, is pumped out into the external space by means of electrode reaction of the pumping cell. As a result, there exists in the measurement-gas space a gradient of concentration of the measurement component in the direction perpendicular to the surface of the first electrode of the pumping cell, that is, in the direction of thickness or depth of the measurement-gas space. In addition, there exists another gradient of concentration of the measurement component in the direction parallel to the surface of the first electrode. Due to these gradients of concentration in the two different directions, the level of an electromotive force to be induced in the sensing cell may not be sufficiently high if the distances "l" and "m" of the first and third electrodes fall within a range represented by the inequality indicated below:

$$0 < m - l < 5w$$

The measurement-gas space may be formed between the electrochemical pumping and sensing cells. Further, the measurement-gas space may communicate with the external space, through a gas-inlet aperture which is formed through a thickness of the electrochemical pumping cell and/or the electrochemical sensing cell, or may be open at its inlet directly to the external space in a direction parallel to the planes of the first and second solid electrolyte bodies. The second electrode of the electrochemical pumping cell may be substantially exposed to the external space, while the fourth electrode of the electrochemical sensing cell may be exposed to a reference-gas space in which a reference gas exists. The second electrode may also be exposed to a reference-gas space.

In a preferred form of the invention, the electrochemical device further includes a suitable heater layer for heating the solid electrolyte bodies of the pumping and sensing cells in order to maintain their operating temperatures at a sufficiently high level for assuring accurate and reliable operation of the electrochemical device, even while the temperature of the measurement gas is not sufficiently high. In this case, the heater layer may be formed in contact with one of the electrochemical pumping and sensing cells.

According to another preferred form of the invention, the first electrode of the pumping cell and/or the third electrode of the sensing cell, which is/are exposed to the measurement-gas space, is/are covered at one of their opposite surfaces by a porous protective layer. In this instance, the first and/or third electrode(s) is/are exposed to an atmosphere in the measurement-gas space, through the respective porous protective layer(s), and thus protected from direct exposure to the measurement gas.

BRIEF DESCRIPTION OF THE DRAWINGS

The foregoing and other objects, features and advantages of the present invention will be better understood from reading the following detailed description of preferred embodiments of the invention, when considered in conjunction with the accompanying drawings, in which.

DETAILED DESCRIPTION OF THE PREFERRED EMBODIMENTS

To further clarify the concept of the prsent invention, preferred arrangements suitable for embodying the invention will be described in detail referring to the accompanying drawing.

Figure 1:
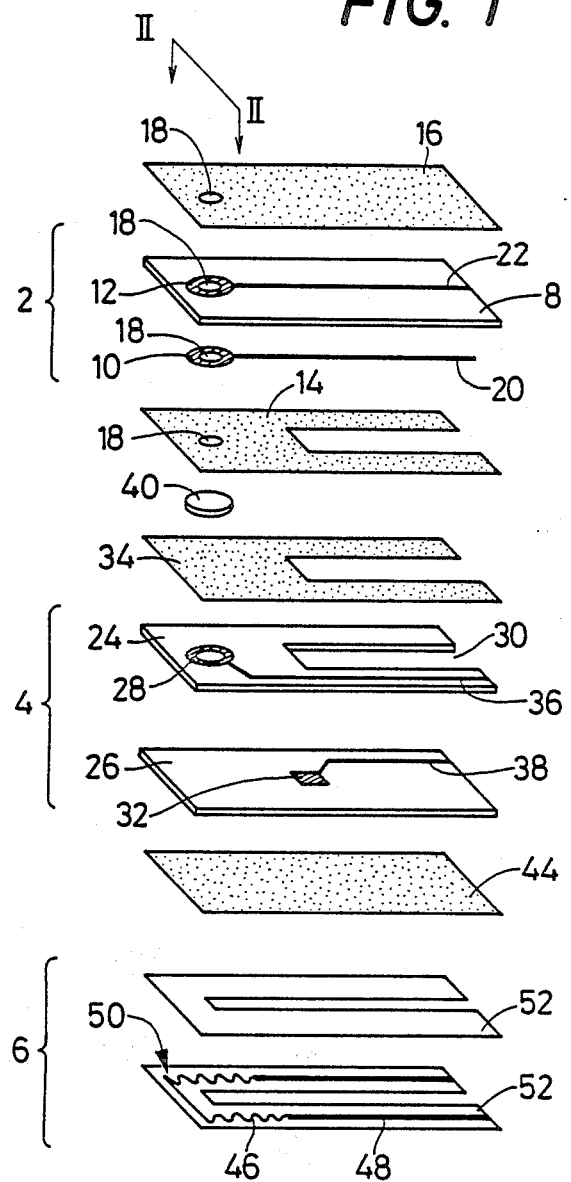
FIG. 1 is an exploded view in perspective of a sensing element of one embodiment of an electrochemical device of this invention in the form of an oxygen sensor.
Figure 2:
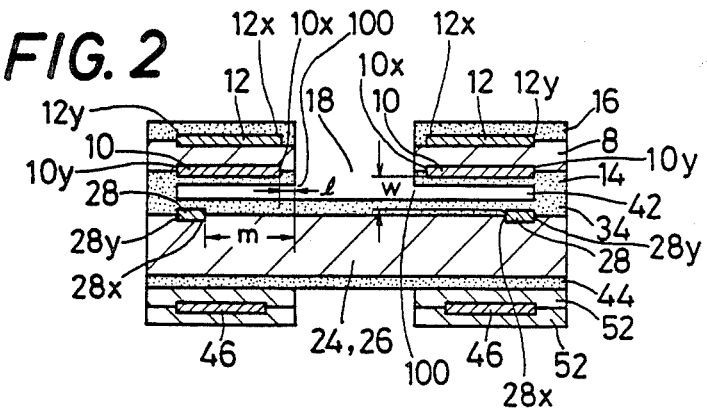
FIG. 2 is an elevational view in cross section taken along line II—II of FIG. 1.

Referring first to an exploded perspective view of FIG. 1 and an elevational cross sectional view of FIG. 2, there is shown an example of a sensing element incorporated in one embodiment of an electrochemical device of the invention in the form of an oxygen sensor. This oxygen sensor is an integral co-fired laminar structure which comprises an electrochemical pumping cell 2, an electrochemical sensing cell 4, and an electrical heater 6 made of ceramics, which are superposed one on another.

The electrochemical pumping cell 2 consists of a planar solid electrolyte body 8 made of a suitable solid electrolyte material such as zirconia ceramics containing yttria, and an inner and an outer pumping electrode 10, 12 which are disposed in contact with opposite surfaces of the solid electrolyte body 8. The inner pumping electrode 10 has an innermost transverse end $10y$ and an outermost transverse end $10x$. Likewise, the outer pumping electrode 12 has an innermost transverse end $12y$ and an outermost transverse end $12x$. The inner and outer pumping electrodes 10, 12 serve as a first and a second electrode of the sensor, respectively. To protect these inner and outer pumping electrodes 10 and 12 from direct exposure to a measurement gas, inner and outer porous protective layers 14, 16 made of alumina or other ceramic materials are formed on the opposite surfaces of the solid electrolyte body 8 so as to cover the electrodes 10, 12.

A gas-inlet aperture 18 is formed through the outer protective layer 16, the outer pumping electrode 12, the solid electrolyte body 8, the inner pumping electrode 10 and the inner protective layer 14. This gas-inlet aperture 18 is designed to introduce the measurement gas into the oxygen sensor. The diameter of the gas-inlet aperture 18 is selected so that a diffusion resistance of the aperture 18 is substantially negligible as compared with that of measurement-gas space. The inner and outer pumping electrodes 10, 12 of the pumping cell 2 are connected through respective electric leads 20, 22 to an external DC power source. With an electric current applied between the pumping electrodes 10, 12, of the pumping cell 2 is operated in such a manner as to move oxygen ions through the solid electrolyte body 8 from the side of the inner pumping electrode 10 toward the outer pumping electrode 12, or vice versa, depending upon the direction of flow of the electric current applied.

In the meantime, the electrochemical sensing cell 4 comprises an air-passage member or spacer layer 24 and a planar solid electrolyte body 26, which are superposed on each other. Like the solid electrolyte body 8 of the pumping cell 2, these spacer layer 24 and solid electrolyte body 26 are made of a solid electrolyte material such as zirconia ceramics containing yttria. On the surface of the spacer layer 24, a measuring electrode 28 in the form of a ring is formed as a third electrode of the oxygen sensor. The ring-shaped electrode 28 has a relatively small radial wall width. Or stated differently, with regard to FIG. 2, the electrode 28 has an innermost transverse end $28y$ and an outermost end $28x$. On the surface of the solid electrolyte body 26, a reference electrode 32 is formed as a fourth electrode of the oxygen sensor. The reference electrode 32 is located so that it is exposed to an atmosphere in a reference-gas space 30. The reference-gas space 30 is defined by a rectangular slot formed in the spacer layer 24, and the upper and lower solid electrolyte bodies 8 and 26 which close the rectangular slot except at its longitudinal end which is open to the ambient air.

The surface of the spacer layer 24 on which the measuring electrode 28 is formed is covered by a thin porous protective layer 34. Thus, the measuring electrode 28 is protected from the measurement gas. An electromotive force is induced between the measuring and reference electrodes 28, 32, due to a difference in oxygen concentration (partial pressure) between the atmospheres to which the electrodes 28, 32 are exposed. The measuring and reference electrodes 28, 32 are connected through respective electric leads 36, 38 to an external measuring device, so that the electromotive force induced between these electrodes is detected by the measuring device.

Between the porous protective layers 14 and 34 disposed adjacent to the electrochemical pumping and sensing cells 2 and 4, respectively, there is provided a circular thermally-disappearing layer 40 which has a relatively small thickness. Upon firing of the sensing element, this layer 40 disappears, whereby there is formed a thin flat measurement-gas space 42 of a small thickness between the two porous protective layers 14, 34, as illustrated in FIG. 2. The thin flat measurement-gas space 42, as viewed in FIG. 2, has a transverse axis running substantially parallel to a horizontal axis of the Figure. The thin flat measurement-gas space 42 is positioned such that the gas-inlet aperture 18 of the pumping cell 2 is open in a substantially radially central portion of the measurement-gas space 42, whereby the measurement gas is introduced into the measurement-gas space 42 through the gas-inlet aperture 18. Since the gas-inlet aperture 18 occupies the central portion of the flat measurement-gas space 42, it is considered, in the interest of each understanding of the invention, that the measurement-gas space 42 has an annular shape as viewed in a direction perpendicular to the surface of the porous protective layer 34.

The ring-shaped measuring electrode 28 of the sensing cell 4 is located in alignment with the radially outermost portion of the annular measurement-gas space 42, as indicated in FIG. 2. The measuring electrode 28 is exposed to the atmosphere in the measurement-gas space 42 through the porous protective layer 34. The ring-shaped inner pumping electrode 10 of the pumping electrode 2 is positioned such that its outer periphery is aligned with the outer periphery of the annular measurement-gas space 42. The inner pumping electrode 10 is exposed to the atmosphere in the measurement-gas space 42 through the porous protective layer 14.

Further, the measurement-gas space 42, the inner pumping electrode 10 and the measuring electrode 28 are dimensioned and positioned relative to each other such that a radial distance "m" between the inlet (inner periphery) of the measurement-gas space 42 and the inner periphery of the measuring electrode 28 is greater than a radial distance "l" between the inlet or inner periphery of the measurement-gas space 42 and the inner periphery of the inner pumping electrode 10, as measured in a cross section perpendicular to planes of the planar solid electrolyte bodies 8, 26.

On the surface of the solid electrolyte body 26 of the sensing cell 4 remote from its surface on which the reference electrode 32 is disposed, there are integrally formed a porous protective layer 44 and the previously indicated electric heater 6 such that the porous protective layer 44 is sandwiched by the solid electrolyte body 26 and the electric heater 6. This electric heater 6 comprises a heating element 50 consisting of a heat-generating portion 46 and electric lead portions 48, and further comprises a pair of ceramic layers 52, 52 which have a high electric resistance and sandwich the heating element 50 therebetween. The heat-generating portion 46 of the electric heater 6 is energized by application of an electric current through the electric lead portions 48 connected to an external power source, so that the solid electrolyte layers (solid electrolyte bodies 8, 26 and spacer layer 24) and the electrodes (10, 12; 28, 32) of the pumping and sensing cells 2, 4 may be held at a proper operating temperature even while the temperature of the measurement gas is lower than necessary for accurate sensing operation of the oxygen sensor.

It is not necessary that the annular flat measurement-gas space 42 has a constant thickness or depth over the entire radial distance between its inner and outer peripheries. Rather, it is preferred that the thickness is increased in steps or continuously in the radially inward direction so that the radially innermost portion has the largest thickness. This arrangement is effective for minimizing an adverse influence of pressure pulsations of exhaust gases from an internal combustion engine, and for shortening an operating response of the oxygen sensor. Generally, it is desired that the thickness or depth of the measurement-gas space 42 be held within a range of 1-100 microns.

As illustrated in FIG. 2 and as previously indicated, the ring-shaped measuring electrode 28 of the sensing cell 4 is positioned relative to the annular measurement-gas space 42 such that the outer periphery of the electrode 28 (i.e., the so-called innermost transverse end 28y) is substantially aligned with the outer periphery of the annular measurement-gas space 42, and such that the inner periphery of the measuring electrode 28 the so-called outermost transverse end 28x) is located a greater distance radially outwardly away from the inlet (inner periphery) of the measurement-gas space 42, than the inner pumping electrode 10 (i.e., the outermost transverse end 10x of the electrode 10 is located closer to the inlet 100 than the outermost transverse end 28x of the electrode 28). In other words, the radial distance "l" between the inner peripheries of the measurement-gas space 42 and the inner pumping electrode 10 is selected to be smaller than the radial distance "m" between the inner peripheries of the measurement-gas space 42 and the measuring electrode 28 (i.e., l<m). Preferably, the radial distances "l" and "m" are determined so as to satisfy the following dimensional relation:

$$m - l \geq 5w,$$

where w: thickness of measurement-gas space 42 (distance between the surfaces of the electrodes 10 and 28 which are exposed to the space 42) at the inner periphery of electrode 28 (at a point of the electrode 28 nearest to the inlet of the space 42)

The above dimensional and positional arrangement of the electrodes 10, 28 makes it possible to minimize a gradient of concentration of a diffused measurement component (oxygen) of the measurement gas within the measurement-gas space 42, in the radial direction of the space 42 (in the horizontal direction of FIG. 2), in order to permit the sensing cell 4 to provide an electromotive force which exactly represents the concentration of the measurement component. Namely, the above arrangement allows accurate determination of the oxygen concentration of the ambient air as the measurement gas, by detecting an electromotive force induced by the sensing cell 4.

While the outer periphery of the inner pumping electrode 10 of the pumping cell 2 is substantially aligned with the outer periphery of the annular measurement-gas space 42, as previously indicated, it is preferred to dimension the inner pumping electrode 10 and the measurement-gas space 42 such that the radial wall width of the inner pumping electrode 10 corresponds to not greater than 70% of the entire volume of the measurement-gas space 42. The above positional and dimensional arrangement of the inner pumping electrode 10 relative to the annular measurement-gas space 42 is also effective for avoiding the adverse influence of the pressure variation (pulsation) of the measurement gas which is introduced into the measurement-gas space 42 through the gas-inlet aperture 18.

In the electrochemical device which is constructed as described hitherto, an electric current is applied between the inner and outer pumping electrodes 10, 12 through the corresponding electric leads 20, 22, to pump out oxygen (measurement component) from the measurement-gas space 42 toward the outer pumping electrode 12 through the solid electrolyte body 8, at a rate corresponding to the amount of electric current applied to the electrodes 10, 12, whereby the measurement component is discharged through the porous protective layer 16 into an external space in which the measurement gas exists. At the same time, an electromotive force is induced between the measuring and reference electrodes 28, 32 of the sensing cell 4 which are exposed to different atmospheres, i.e., to the atmosphere in the measurement-gas space 42 and to the reference gas, respectively. The electromotive force induced is measured by, for example, an external voltmeter through the electric leads 36, 38. The concentration of the measurement component (oxygen concentration) in the measurement-gas space 42 may be determined based on the electric current applied to the pumping cell 2 and on the electromotive force induced in the sensing cell 4.

In the meantime, oxygen in the measurement gas is introduced into the measurement-gas space 42 through the gas-inlet aperture 18, to compensate for the amount of oxygen which is pumped out through an oxygen pumping action of the pumping cell 2 with an electric current applied to their electrodes 10, 12. However, since the supply of oxygen into the measurement-gas space 42 is limited by the small thickness or depth of the thin flat space 42, the oxygen partial pressure in the space 42 is made lower than that of the measurement gas in the external space. Therefore, the oxygen sensor may be advantageously used for a measurement gas whose oxygen partial pressure is relatively high. For example, the illustrated oxygen sensor may be suitably used for controlling an engine which emits so-called "lean-burned" exhaust gases whose oxygen partial pressure is higher than that of the exhaust gases which are produced in combustion of an air-fuel mixture of the stoichiometric air/fuel ratio.

Of course, the illustrated electrochemical sensing element may be used for determining the oxygen concentration in exhaust gases which are produced as a result of combustion of an air-fuel mixture of the stoichiometric air/fuel ratio. In this instance, the measurement is effected based only on the electromotive force induced between the measuring and reference electrodes 28, 32 of the sensing cell 4, without relying on the oxygen pumping function of the pumping cell 2.

Further, the instant electrochemical sensing element may also be used as a so-called "rich-burn" sensor for detecting "rich-burned" exhaust gases containing large amounts of unburned components. The rich-burned exhaust gases are produced in combustion of a fuel-rich air-fuel mixture, and have an oxygen partial pressure which is lower than that of the exhaust gases produced in combustion of an air-fuel mixture of the stoichiometric air/fuel ratio. The rich-burn sensor may sense the combustion condition of an engine which produces such rich-burned exhaust gases containing unburned components.

The solid electrolyte layers (8, 24 and 26) which are major components of the electrochemical pumping and sensing cells 2, 4 may be made of $SrCeO_3$, solid solution of bismuth oxide-oxide of rare earth element, $La_{1-x}Ca_xYO_{3-\alpha}$, in place of previously indicated zirconia ceramics which is preferably used.

The electrochemical sensing element as described above may be manufactured in a suitable known manner, for example, by superposing laminar green structures of the pumping and sensing cells 2, 4 and the heater 6. In this case, each of the laminar green structures of the cells 2, 4 may be formed by screen-printing unfired layers of the electrodes, electric leads and/or porous protective layer or layers, on the appropriate surfaces of a green sheet of the solid electrolyte body 8, 26. The prepared laminar green structures of the two cells 2, 4 are superposed on each other, and then on a green structure of the heater 6. The finally obtained laminar stack of the cells 2, 4 and the heater 6 is then co-fired into the desired electrochemical sensing element.

In preparing the laminar green assembly of the cells 2, 4, the thermally-disappearing layer 40 made of a suitable material such as paper or thermo-setting resin is interposed between the green layers of the porous protective layers 14, 34. This thermally-disappearing layer 40 disappears during firing of the laminer green structure of the sensing element. Thus, there is formed the previously discussed annular flat measurement-gas space 42 having the predetermined diffusion resistance. If desired, the measurement-gas space 42 may be filled with a suitable porous ceramic layer which provides the predetermined diffusion resistance. In this instance, the mechanical strength of the measurement-gas space 42 is increased.

In the case where the electrochemical element is produced in a co-firing process, it is preferred to co-fire the unfired layers of the electrodes 10, 12, 28, 32, and their electric leads 20, 22, 36, 38. In this case, these unfired layers are formed by printing, preferably by using as their major components at least one element selected from the platinum group which includes platinum, palladium, iridium, ruthenium, rhodium and osmium. In this respect, it is desired to admix fine ceramic particles of zirconia, yttria, alumina, etc. with the materials of the electrodes and leads, for preventing flake-off and breakage. The addition of such ceramic particles improves the adhesion of the electrodes and leads to the contacting layers.

While the present invention has been described in its preferred embodiment, it is to be understood that the invention is not confined to the details of the foregoing arrangement. For example, the invention may be embodied in modified forms as illustrated in FIGS. 3 through 8.

Figure 4:
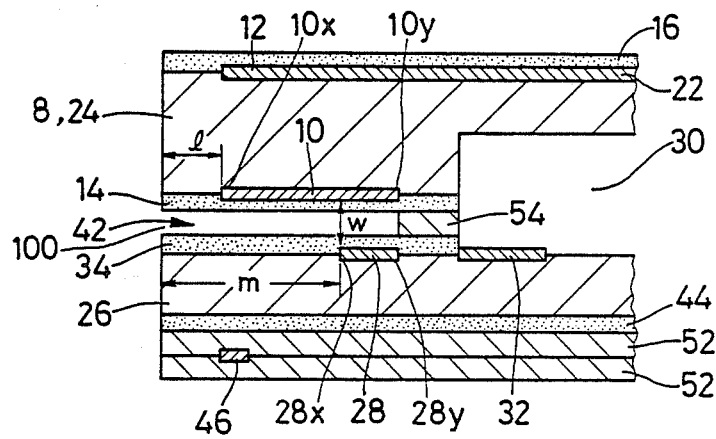
FIGS. 4, 6 and 8 are elevational cross sectional views taken along lines IV—IV, VI—VI and VIII—VIII of FIGS. 3, 5 and 7, respectively.
Figure 3:
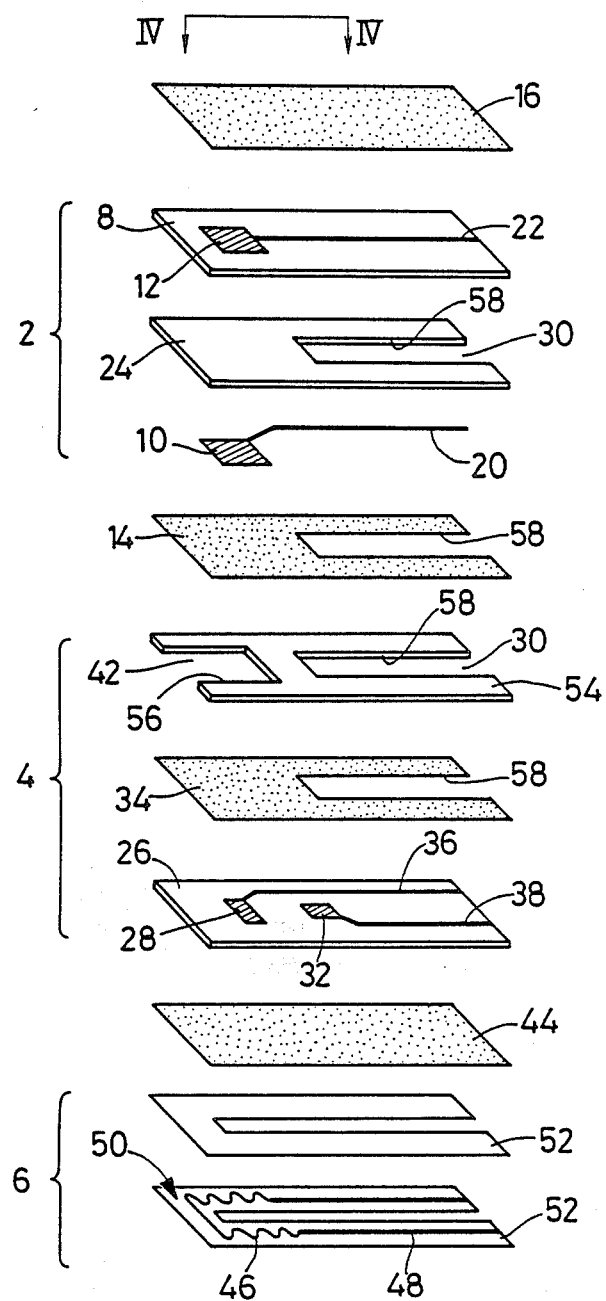
FIGS. 3, 5 and 7 are exploded views corresponding to FIG. 1, showing modified embodiments of the electrochemical oxygen sensor of the invention.

In the modified embodiment of FIGS. 3-4 of an electrochemical device of the invention as an oxygen sensor, the thin flat measurement-gas space 42 is rectangular in shape and open at one longitudinal end of the sensing element, unlike the annular measurement-gas space 42 of the preceding embodiment. That is, the instant rectangular measurement-gas space 42 communicates directly with an external space in which the measurement gas exists through an inlet 100 which is located along the transverse axis of the measurement-gas space 42. The measurement gas is introduced into the measurement-gas space 42 through its open end (inlet 100), and the measurement component is diffused toward the innermost end of the measurement-gas space 42 opposite to the open end, with a predetermined diffusion resistance which is given by the small thickness or depth of the space 42. In this modified embodiment, the measuring electrode 28 is rectangular in shape and has an innermost transverse end 28y which is aligned with the innermost portion of the measurement-gas space 42 such that the electrode 28 extends parallel to the innermost edge of the rectangular space 42 (perpendicular to the longitudinal direction of the sensing element i.e., along the so-called transverse direction). With this arrangement, the measuring electrode 28 is exposed to the measurement component existing in the innermost portion of the rectangular measurement-gas space 42, through the porous structure of the porous protective layer 34.

The rectangular measurement-gas space 42 is formed in a spacer layer 54 which is interposed between the electrochemical pumping and sensing cells 2, 4. More particularly, the spacer layer 54 has a rectangular cutout 56 which is formed in one of its opposite longitudinal end portions. The rectangular cutout 56 is open in the corresponding longitudinal end of the spacer layer 54, and closed by the upper spacer layer 24 and the lower solid electrolyte body 26. Thus, the spacer layers 24, 54 and the solid electrolyte body 26 cooperate to define the thin flat rectangular measurement-gas space 42 which has the predetermined diffusion resistance and is open at one longitudinal end of the spacer member 54, in the direction parallel to the surfaces of the planar solid electrolyte body 26.

In the other longitudinal end portion of the spacer layer 54 opposite to the end portion in which the rectangular cutout 56 is provided, there is formed an elongate cutout 58. Similar elongate cutouts 58 are formed in the corresponding portions of the spacer layer 24 and porous protective layers 14, 34. All of these elongate cutouts 58 cooperate with the upper and lower planar solid electrolyte bodies 8, 26 to define the previously indicated reference-gas space 30 which is open at its one end for introducing therein the ambient air as a reference gas.

In this embodiment, too, the inner pumping electrode 10 of the pumping cell 2 is exposed to the atmosphere in the rectangular measurement-gas space 42 through the porous protective layer 14. This inner pumping electrode 10 is positioned in alignment with the inner portion of the rectangular measurement-gas space 42, and is dimensioned so that the surface area of the electrode 10 exposed to the atmosphere in the space 42 is not greater than 70% of the total volume of the space 42. Further, as shown in FIG. 4, the inner pumping electrode 10 has an innermost transverse end 28y and an outermost transverse end 28x and the measuring electrode 28 is positioned and dimensioned relative to each other the inner pumping electrode 10 so that a distance "m" between the inlet 100 (open end) of the space 42 and the outermost transverse end 28x of the measuring electrode 28 (the edge nearest to the inlet 100 of the space 42) is larger than a corresponding distance "l" of the inner pumping electrode 10. The inner pumping electrode 10 is disposed with its transverse length parallel to the inner edge of the rectangle of the measurement-gas space 42 (perpendicular to the length of the spacer layer 54).

Since the measuring electrode 28 of the sensing cell 4 is positioned relative to the inner pumping electrode 10 of the pumping cell 2 so that the distance "l" is smaller than the distance "m" as described above, the concentration of the measurement component in the measurement gas from the external space is reduced due to the pumping action of the pumping cell 4, as the measurement component is diffused into the measurement-gas space 42. The concentration of the component is made sufficiently low in the innermost portion of the rectangular measurement-gas space 42 adjacent to the measuring electrode 28. Thus, a relatively high level of electromotive force is induced between the measuring electrode 28 and the reference electrode 32 due to a difference in concentration of the measurement component between the measurement gas in the innermost portion of the measurement-gas space 42, and the reference ambient air in the reference-gas space 30.

Like the preceding embodiment, the present modified embodiment is adapted such that the thin flat measurement-gas space 42 and the reference-gas space 30 are located in substantially the same plane parallel to the surfaces of the planar solid electrolyte bodies 8, 26. Consequently, the thickness of the pumping and sensing cells 2, 4 and consequently the overall thickness of the electrochemical sensing element are effectively reduced, and the overall size of the sensing element may be minimized. Further, the reduced thickness of the sensing element assures a reduced temperature gradient in the direction of thickness of the element, which is conducive to the protection of the solid electrolyte bodies and consequently of the sensing element from damage or breakage due to thermal stresses. In addition, the reduction in thickness of the sensing element permits shortening of a time that is required by the heater to heat the cells to their operating temperature.

The pumping and sensing cells 2, 4 are electrically insulated from each other by the porous protective layers 14, 34, whereby the sensing cell 4 is suitably protected from the influence of a leaking current from the pumping cell 2. This electric insulation provides an improvement in the accuracy of detection of an electromotive force by the sensing cell 4. For this purpose, the porous protective layers 14, 34 are made of a ceramic material having a high electric resistance. However, the spacer layer 54 may be made of a highly electrically resistive ceramic material, so as to serve as an insulating layer, in addition to or in place of the porous protective ceramic layers 14, 34.

Figure 6:
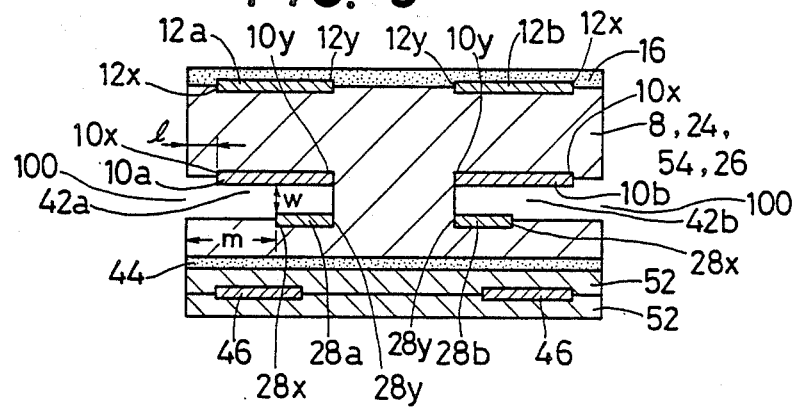
Figure 5:
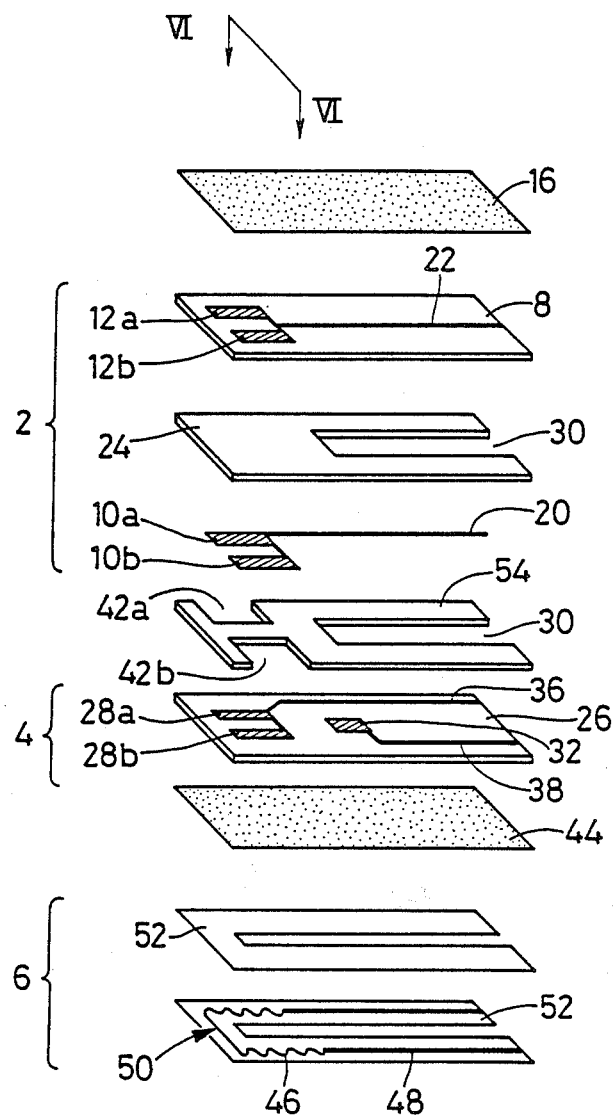

Referring next to FIGS. 5-6, there is shown a third embodiment of the invention as an oxygen sensor, which is similar to the preceding two embodiments, in that the electrochemical pumping and sensing cells 2, 4 and the electrical heater 6 constitute a laminar structure of the sensing element. However, the instant arrangement is different from the preceding two arrangements in that two thin flat spaces 42a, 42b are provided to serve as a measurement-gas space which provides a predetermined diffusion resistance. Described in more detail, the two thin flat transverse measurement-gas spaces 42a, 42b are formed in the spacer layer 54 in a spaced-apart and symmetric relation with each other such that the two spaces 42a, 42b are open to the external space at the transversely opposite sides of the spacer layer 54. In this embodiment, a measuring electrode is provided in the form of a pair of electrodes 28a, 28b which are aligned with the innermost portions of the respective flat spaces 42a, 42b.

In this modified embodiment, a pair of inner pumping electrodes 10a, 10b of the pumping cell 2 are disposed such that they are exposed to the inner portions of the respective flat spaces 42a, 42b. Similarly, a pair of outer pumping electrodes 12a, 12b are positioned in alignment with the inner pumping electrodes 10a, 10b.

In the present embodiment, too, the inner pumping electrodes 10a, 10b and the measuring electrodes 28a, 28b which are exposed to the corresponding thin flat rectangular measurement-gas spaces 42a, 42b, are positioned and dimensioned with respect to each other, such that the distance "l" of the inner pumping electrodes 10a, 10b is smaller than the distance "m" of the measuring electrodes 28a, 28b, as indicated in FIG. 6. This positional and dimensional arrangement permits the detection of an effective electromotive force induced by the sensing cell 4.

Figure 7:
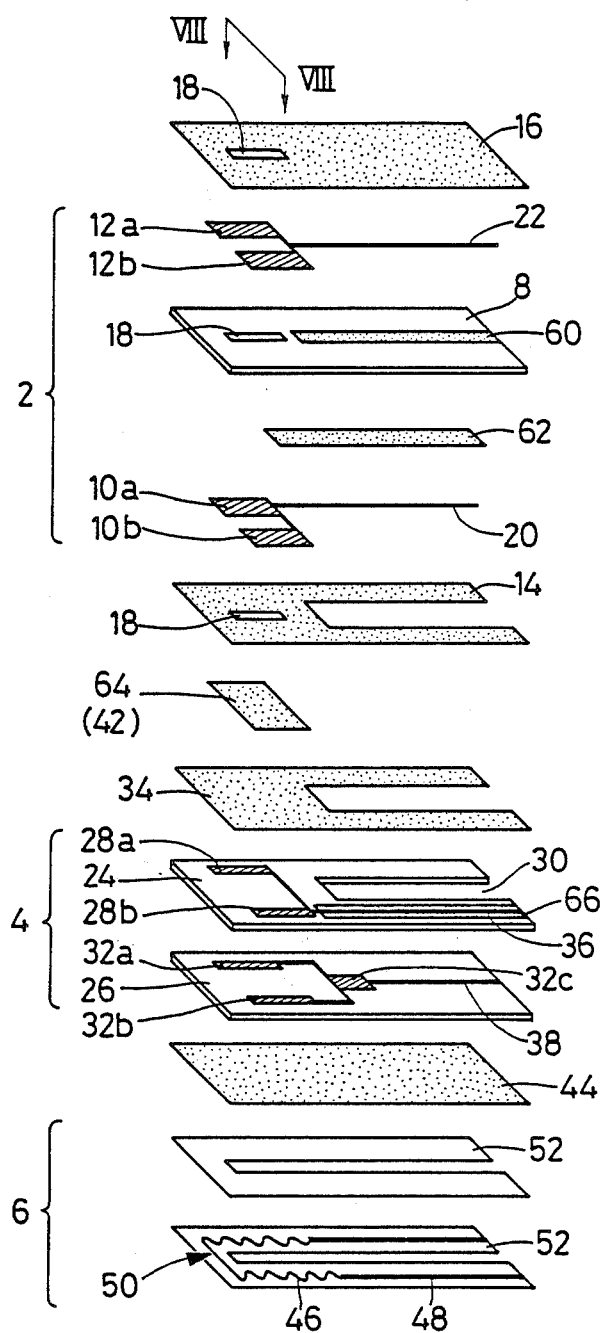
Figure 8:
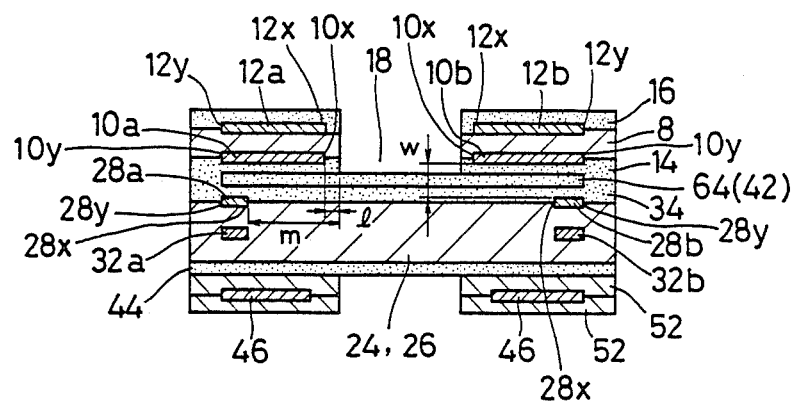
Figure 9:
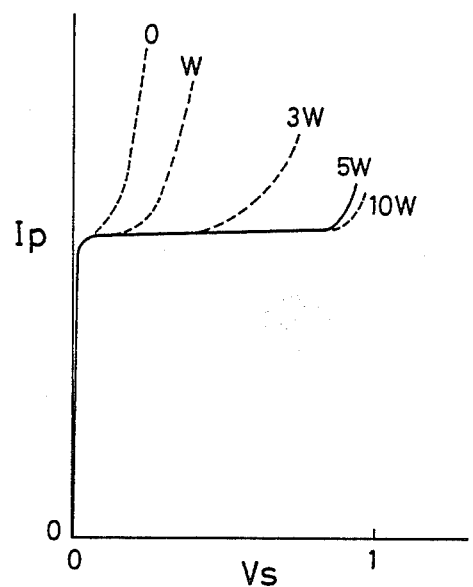
FIG. 9 is a graph illustrating a relation between a pumping current Ip applied to an electrochemical pumping cell of the oxygen sensor, and an electromotive force induced in an electrochemical sensing cell of the sensor, when an ambient air is applied as a measurement gas to the oxygen sensor.

Referring to FIGS. 7 and 8, there is shown a fourth embodiment of the invention, which is a modification of the oxygen sensor of the first embodiment of FIG. 1. This modified oxygen sensor is characterized by the gas-inlet aperture 18 formed through the pumping cell 2. That is, the aperture 18 of FIGS. 7-8 has an elongate rectangular shape, contrary to the aperture 18 of FIG. 1. The outer pumping electrodes 12a, 12b, and the inner pumping electrodes 10a, 10b, are positioned on opposite long sides of the rectangle of the rectangular aperture 18. Reference numerals 60, 62 indicate porous insulating layers for insulating the electric leads 22, 20 of the pumping electrodes 12a, 12b, 10a, 10b.

To form the measurement-gas space 42, a rectangular porous diffusion-resisitance layer 64 having a predetermined diffusion resistance is interposed between the porous protective layers 14, 34, such that the rectangle of the diffisuion-resistance layer 64 extends along the width of the porous protective layers 14, 34. The rectangular gas-inlet aperture 18 is aligned with the longitudinally central portion of the rectangular porous diffusion-resistance layer 64. Thus, the porous structure of the diffusion-resistance layer 64 communicates with the gas-inlet aperture 18.

Although the gas-inlet aperture 18 of the instant embodiment is formed only through the pumping cell 2, it is possible to form the aperture 18 through the sensing cell 4, or both of the pumping and sensing cells 2, 4. At any rate, the aperture 18 should be formed so as to communicate with the thin flat measurement-gas space 42 in the form of the porous diffusion-resistance layer 64.

As described above, the rectangular thin flat porous structure of the diffusion-resistance layer 64 is formed so as to extend transversely of the cells 2, 4, and the gas-inlet aperture 18 is open to the central portion of the diffusion-resistance layer 64. In the meantime, the two measuring electrodes 28a, 28b are disposed on the spacer layer 24 so that the electrodes 28a, 28b are aligned with the opposite end portions of the rectangle of the diffusion-resistance layer 64. The electric lead 36 connected to the measuring electrodes 28a, 28b is electrically insulated from the spacer layer 24 by a porous insulating layer 66.

Further, two electrodes 32a, 32b are disposed on the solid electrolyte body 26 so that they are positioned opposite to the corresponding measuring electrodes 28a, 28b. That is, the measuring electrodes 28a, 28b, and the electrodes 32a, 32b are disposed on the opposite surfaces of the spacer layer 24, in alignment with each other. Further, an electrode 32c is disposed on the solid electrolyte body 26 so that it is exposed to the reference-gas space 30. These three electrodes 32a, 32b and 32c are electrically connected to each other, and cooperate to constitute the reference electrode of the sensing cell 4. In this arrangement wherein the reference electrode 32 comprises the two electrodes 32a, 32b aligned with the measuring electrodes 28a, 28b, the impedance of the sensing cell 4 is reduced, and its detecting performance is improved.

In this modified oxygen sensor, too, the diffusion-resistance layer 64, inner pumping electrodes 10a, 10b and measuring electrodes 28a, 28b are positioned and dimensioned with respect to each other, so that the distance "l" between the inner edge of the inner pumping electrode 28a, 28b and the adjacent side of the rectangle of the gas-inlet aperture 18 (inlet of the space 42) is smaller than the corresponding distance "m" of the meauring electrode 32a, 32b. This arrangement provides the same advantage as previously discussed.

While the present invention has been described in its preferred embodiments for illustrative purpose only, it is to be understood that the invention is not limited to the details of the illustrated construction and arrangement, but may be otherwise embodied with various changes, modifications and improvements which may occur to those skilled in the art, without departing from the spirit of the present invention.

Although the electrochemical device according to the invention is suitably used as a lean-burn sensor as illustrated, the device may be used as a sensor for detecting exhaust gases which are produced in combustion of an air-fuel mixture having an air/fuel ratio substantially equal to the stochiometric ratio. Further, the electrochemical device of the invention may also be suitably utilized as a rich-burn sensor for handling fuel-rich exhaust gases which are produced as a result of combustion of a fuel-rich air-fuel mixture. Furthermore, the present invention may be embodied as various sensors or controllers for determining or controlling the concentration of specific components of a measurement gas which are associated with electrode reaction, such as nitrogen, carbon dioxide and hydrogen, other than oxygen.

As is apparent from the foregoing description, the electrochemical device constructed according to the present invention is characterized in that the first electrode of the electrochemical pumping cell is positioned closer to the inlet or open end of the measurement-gas space, than the third electrode of the electrochemical sensing cell, whereby the sensing cell is least influenced by a gradient of concentration of a measurement component, such as oxygen, in the measurement gas which is diffused into the measurement-gas space through its inlet, even when the ambient air is used as a test gas (measurement gas) for testing the electrochemical device. Consequently, a relatively high level of electromotive force is obtained in the sensing cell, and the detecting accuracy of the sensing cell is accordingly improved. Therefore, it is possible to accurately adjust the electrochemical device based on the obtained electromotive force. Described more specifically, the present invention has made it possible to use the ambient air for testing the electrochemical pumping cell, during a process of manufacture of the electrochemical device, or for periodically checking and adjusting the pumping cell after the electrochemical device is installed on an automotive vehicle. These are industrially significant aspects of the present invention.

What is claimed is:

1. An electrochemical device for determining the concentration of a component in a measurement gas, comprising:

a plurality of superposed planar layers;

an electrochemical pumping cell including a first planar solid electrolyte body and at least a first electrode and a second electrode disposed in contact with said first planar solid electrolyte body, said first electrode having an innermost transverse end and an outermost transverse end;

an electrochemical sensing cell including a second planar solid electrolyte body, and a third electrode and a fourth electrode disposed in contact with said second planar solid electrolyte body, said third electrode having an innermost transverse end and an outermost transverse end; and means for defining a transverse measurement-gas space having a transverse axis, said measurement-gas space communicating with an external space in which the measurement gas exists through an inlet opening, said inlet opening and transverse measurement-gas space having a predetermined diffusion resistance to said component in the measurement gas which is to be measured, said first electrode of the electrochemical pumping cell and said third electrode of the electrochemical sensing cell communicating with said measurement-gas space, wherein said outermost transverse end of said first electrode is located a distance "l" from said inlet along said transverse axis and said outermost transverse end of said third electrode is located a distance "m" from said inlet along said transverse axis, and said first and third electrodes are located on opposite sides of said measurement-gas space and are separated by a distance "w", such that the following relationship is satisfied:

$$m - l \geq 5w,$$

such that an average oxygen concentration along a transverse direction of said third electrode in communication with said measurement-gas space is less than an average oxygen concentration along a transverse direction of said first oxygen concentration along a transverse direction of said first electrode in communication with said measurement-gas space.

2. The electrochemical device of claim 1, wherein said measurement-gas space is formed between said electrochemical pumping cell and said electrochemical sensing cell.

3. The electrochemical device of claim 1, wherein said inlet opening is formed through a thickness of said electrochemical pumping cell or through a thickness of said sensing cell.

4. The electrochemical device of claim 1, wherein said measurement-gas space is open at said opening inlet directly to said external space along said transverse axis of the measurement gas space.

5. The electrochemical device of claim 1, wherein said second electrode of the electrochemical pumping cell is substantially exposed to said external space, and said fourth electrode of the electrochemical sensing cell is exposed to a reference-gas space in which a reference gas exists.

6. The electrochemical device of claim 1, wherein said second electrode of the electrochemical pumping cell and said fourth electrode of the electrochemical sensing cell are exposed to a reference-gas space in which a reference gas exists.

7. The electrochemical device of claim 1, wherein a porous ceramic layer having said predetermined diffusion resistance is located in said measurement-gas space.

8. The electrochemical device of claim 1, wherein said first electrode is covered by a porous protective layer along a surface which is exposed to said measurement-gas space, and is exposed to said measurement gas through said porous protective layer.

9. The electrochemical device of claim 1, wherein said third electrode is covered by a porous protective layer along a surface which is exposed to said measurement-gas space, and is exposed to said measurement gas through said porous protective layer.

10. The electrochemical device of claim 1, further including a heater layer formed in contact at least one of said electrochemical pumping and sensing cells.

11. The electrochemical device of claim 1, wherein said inlet opening is formed through a thickness of said electrochemical pumping cell and through a thickness of said sensing cell.

12. An electrochemical device for determining the concentration of a component in a measurement gas, comprising:

a plurality of superposed planar layers;

an electrochemical pumping cell including a first planar solid electrolyte body and at least a first electrode and a second electrode disposed in contact with said first planar solid electrolyte body, said first electrode having an innermost transverse end and an outermost transverse end;

an electrochemical sensing cell including a second planar solid electrolyte body, and a third electrode and a fourth electrode disposed in contact with said second planar solid electrolyte body, said third electrode having an innermost transverse end and an outermost transverse end; and means for defining a transverse measurement-gas space having a transverse axis, said measurement-gas space communicating with an external space in which the measurement gas exists through an inlet opening, said inlet opening and transverse measurement-gas space having a predetermined diffusion resistance to said component in the measurement gas which is to be measured, said first electrode of the electrochemical pumping cell and said third electrode of the electrochemical sensing cell communicating with said measurement-gas space, wherein said outermost transverse end of said first electrode is located a distance "l" from said inlet along said transverse axis and said outermost transverse end of said third electrode is located a distance "m" from said inlet along said transverse axis, and said first and third electrodes are located on opposite sides of said measurement-gas space and are separated by a distance "w", such that the following relationship is satisifed:

$$m - l \geq 5w,$$

such that an average oxygen concentration along a transverse direction of said first electrode in communication with said measurement-gas space is intermediate between an average oxygen concentration within said transverse measurement-gas space and an average oxygen concentration along a transverse direction of said third electrode in communication with said measurement-gas space.

13. The electrochemical device of claim 12, wherein said measurement-gas space is formed between said electrochemical pumping cell and said electrochemical sensing cell.

14. The electrochemical device of claim 12, wherein said inlet opening is formed through a thickness of said electrochemical pumping cell or through a thickness of said sensing cell.

15. The electrochemical device of claim 12, wherein said inlet opening is formed through a thickness of said electrochemical pumping cell and through a thickness of said sensing cell.

16. The electrochemical device of claim 12, wherein said measurement-gas space is open at said opening inlet directly to said external space along said transverse axis of the measurement gas space.

17. The electrochemical device of claim 12, wherein said second electrode of the electrochemical pumping cell is substantially exposed to said external space, and said fourth electrode of the electrochemical sensing cell is exposed to a reference-gas space in which a reference gas exists.

18. The electrochemical device of claim 12, wherein said second electrode of the electrochemical pumping cell and said fourth electrode of the electrochemical sensing cell are exposed to a reference-gas space in which a reference gas exists.

19. The electrochemical device of claim 12, wherein a porous ceramic layer having said predetermined diffusion resistance is located in said measurement-gas space.

20. The electrochemical device of claim 12, wherein said first electrode is covered by a porous protective layer along a surface which is exposed to said measurement-gas space, and is exposed to said measurement gas through said porous protective layer.

21. The electrochemical device of claim 12, wherein said third electrode is covered by a porous protective layer along a surface which is exposed to said measurement-gas space, and is exposed to said measurement gas through said porous protective layer.

22. The electrochemical device of claim 12, further including a heater layer formed in contact with at least one of said electrochemical pumping and sensing cells.

* * * * *